US008052666B2

(12) United States Patent
Sawyer et al.

(10) Patent No.: US 8,052,666 B2
(45) Date of Patent: Nov. 8, 2011

(54) FASTENING SYSTEM HAVING ELASTOMERIC ENGAGING ELEMENTS AND DISPOSABLE ABSORBENT ARTICLE MADE THEREWITH

(75) Inventors: Lawrence H. Sawyer, Neenah, WI (US); Robert L. Popp, Hortonville, WI (US); Joseph D. Coenen, Kaukauna, WI (US); Michael J. Faulks, Neenah, WI (US); Christopher P. Olson, Neenah, WI (US); James M. Carr, Kaukauna, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1238 days.

(21) Appl. No.: 11/026,879

(22) Filed: Dec. 30, 2004

(65) Prior Publication Data

US 2006/0149210 A1    Jul. 6, 2006

(51) Int. Cl.
*A61F 13/15* (2006.01)
(52) U.S. Cl. .......... 604/391; 604/387; 604/386
(58) Field of Classification Search .......... 604/391, 604/387, 386
See application file for complete search history.

(56) References Cited

U.S. PATENT DOCUMENTS

| | | | |
|---|---|---|---|
| 3,692,618 A | 9/1972 | Dorschner et al. | |
| 3,708,361 A | 1/1973 | Stumpf | |
| 3,802,817 A | 4/1974 | Matsuki et al. | |
| 3,849,241 A | 11/1974 | Butin et al. | |
| 3,855,046 A | 12/1974 | Hansen et al. | |
| 4,100,324 A | 7/1978 | Anderson et al. | |
| 4,107,364 A | 8/1978 | Sisson | |
| 4,209,563 A | 6/1980 | Sisson | |
| 4,340,563 A | 7/1982 | Appel et al. | |
| 4,488,928 A | 12/1984 | Ali Khan et al. | |
| 4,640,726 A | 2/1987 | Sallee et al. | |
| 4,663,220 A | 5/1987 | Wisneski et al. | |
| 4,704,116 A | 11/1987 | Enloe | |
| 4,705,710 A | 11/1987 | Matsuda | |
| 4,725,473 A | 2/1988 | Van Gompel et al. | |
| 4,761,318 A | 8/1988 | Ott et al. | |
| 4,795,668 A | 1/1989 | Krueger et al. | |
| 4,818,464 A | 4/1989 | Lau | |
| 4,834,742 A * | 5/1989 | Wilson et al. .......... | 604/389 |
| 4,940,464 A | 7/1990 | Van Gompel et al. | |
| 4,984,339 A | 1/1991 | Provost et al. | |

(Continued)

FOREIGN PATENT DOCUMENTS

DE    196 47 459 A1    5/1998

(Continued)

OTHER PUBLICATIONS

American Society for Testing Materials (ASTM) Designation: D1894-00, "Standard Test Method for Static and Kinetic Coefficients of Friction of Plastic Film and Sheeting," pp. 1-6, published Oct. 2000.

*Primary Examiner* — Jacqueline F. Stephens
(74) *Attorney, Agent, or Firm* — H. Michael Kubicki

(57) ABSTRACT

An improved mechanical fastening system that includes a male component and a female component is disclosed. The female component is adapted for releasable engagement with the male component, and the female component comprises a fibrous web, wherein the fibrous web comprises a layer of elastomeric fibers. A disposable absorbent article employing the improved mechanical fastening system is also disclosed.

30 Claims, 7 Drawing Sheets

U.S. PATENT DOCUMENTS

| | | | |
|---|---|---|---|
| 5,032,122 A | | 7/1991 | Noel et al. |
| 5,046,272 A | | 9/1991 | Vogt et al. |
| 5,104,116 A | | 4/1992 | Pohjola |
| 5,108,820 A | | 4/1992 | Kaneko et al. |
| 5,224,405 A | | 7/1993 | Pohjola |
| 5,226,992 A | | 7/1993 | Morman |
| 5,242,436 A | * | 9/1993 | Weil et al. .............. 604/385.29 |
| 5,271,982 A | | 12/1993 | Verpoest et al. |
| 5,272,236 A | | 12/1993 | Lai et al. |
| 5,278,272 A | | 1/1994 | Lai et al. |
| 5,326,612 A | | 7/1994 | Goulait |
| 5,332,613 A | | 7/1994 | Taylor et al. |
| 5,336,552 A | | 8/1994 | Strack et al. |
| 5,339,499 A | | 8/1994 | Kennedy et al. |
| 5,350,624 A | | 9/1994 | Georger et al. |
| 5,380,313 A | | 1/1995 | Goulait et al. |
| 5,382,400 A | | 1/1995 | Pike et al. |
| 5,425,987 A | | 6/1995 | Shawver et al. |
| 5,470,639 A | | 11/1995 | Gessner et al. |
| 5,539,056 A | | 7/1996 | Yang et al. |
| 5,540,992 A | | 7/1996 | Marcher et al. |
| 5,547,531 A | * | 8/1996 | Allen et al. .................. 156/164 |
| 5,595,567 A | | 1/1997 | King et al. |
| 5,596,052 A | | 1/1997 | Resconi et al. |
| 5,615,460 A | | 4/1997 | Weirich et al. |
| 5,620,779 A | | 4/1997 | Levy et al. |
| 5,624,427 A | | 4/1997 | Bergman et al. |
| 5,669,900 A | | 9/1997 | Bullwinkel et al. |
| 5,681,302 A | * | 10/1997 | Melbye et al. .............. 604/373 |
| 5,683,787 A | | 11/1997 | Boich et al. |
| 5,707,707 A | | 1/1998 | Burnes et al. |
| 5,735,840 A | | 4/1998 | Kline et al. |
| 5,766,389 A | | 6/1998 | Brandon et al. |
| 5,795,350 A | | 8/1998 | Schmitz |
| 5,853,635 A | | 12/1998 | Morell et al. |
| 5,858,515 A | | 1/1999 | Stokes et al. |
| 5,888,607 A | | 3/1999 | Seth et al. |
| 5,897,547 A | | 4/1999 | Schmitz |
| 5,921,977 A | | 7/1999 | Schmitz |
| 5,925,027 A | | 7/1999 | Schmitz |
| 5,932,497 A | | 8/1999 | Morman et al. |
| 5,935,512 A | | 8/1999 | Haynes et al. |
| 5,968,031 A | | 10/1999 | Schmitz |
| 5,997,981 A | | 12/1999 | McCormack et al. |
| 5,997,989 A | | 12/1999 | Gessner et al. |
| 6,015,764 A | | 1/2000 | McCormack et al. |
| 6,111,163 A | | 8/2000 | McCormack et al. |
| 6,164,950 A | | 12/2000 | Barbier et al. |
| 6,217,693 B1 | | 4/2001 | Pelham |
| 6,225,243 B1 | | 5/2001 | Austin |
| 6,245,401 B1 | | 6/2001 | Ying et al. |
| 6,329,016 B1 | | 12/2001 | Shepard et al. |
| 6,342,285 B1 | | 1/2002 | Shepard et al. |
| 6,461,457 B1 | | 10/2002 | Taylor et al. |
| 6,598,276 B2 | | 7/2003 | Shepard et al. |
| 6,712,921 B2 | | 3/2004 | Mitsuno et al. |
| 6,756,327 B2 | | 6/2004 | Martin |
| 6,783,834 B2 | | 8/2004 | Shepard et al. |
| 2002/0037390 A1 | | 3/2002 | Shepard et al. |
| 2002/0037678 A1 | | 3/2002 | Ohata |
| 2002/0160143 A1 | | 10/2002 | Shepard et al. |
| 2003/0124303 A1 | | 7/2003 | Price et al. |
| 2004/0072491 A1 | | 4/2004 | Gillette et al. |
| 2004/0102749 A1 | | 5/2004 | Olson et al. |
| 2004/0110442 A1 | | 6/2004 | Rhim et al. |
| 2004/0158957 A1 | | 8/2004 | Horn et al. |
| 2006/0148359 A1 | | 7/2006 | Van Gompel et al. |

FOREIGN PATENT DOCUMENTS

| | | |
|---|---|---|
| EP | 0 265 739 A1 | 5/1988 |
| EP | 0 217 032 B1 | 2/1992 |
| EP | 0 420 256 B1 | 5/1995 |
| EP | 1 069 223 A1 | 1/2001 |
| EP | 1 350 879 A1 | 10/2003 |
| JP | 07-300752 A | 11/1995 |
| JP | 10-259560 A | 9/1998 |
| JP | 2000-160464 A | 6/2000 |
| JP | 2000-239958 A | 9/2000 |
| JP | 2001-089964 A | 4/2001 |
| WO | WO 95/17111 A1 | 6/1995 |
| WO | WO 96/03101 A1 | 2/1996 |
| WO | WO 97/23348 A2 | 7/1997 |
| WO | WO 98/52458 A1 | 11/1998 |
| WO | WO 00/39201 A2 | 7/2000 |
| WO | WO 03/057118 A1 | 7/2003 |
| WO | WO 03/057119 A2 | 7/2003 |
| WO | WO 03/057121 A1 | 7/2003 |

\* cited by examiner

FASTENING SYSTEM HAVING ELASTOMERIC ENGAGING ELEMENTS AND DISPOSABLE ABSORBENT ARTICLE MADE THEREWITH

BACKGROUND

Releasable, refastenable mechanical fastening systems are common in today's society. For example, mechanical fasteners, sometimes referred to as hook and loop fasteners, are useful in wearable garments, such as disposable absorbent articles, such as diapers, training pants, incontinence products, and feminine care products. Mechanical fasteners can offer a variety of functional benefits to such products, such as the ability to fasten the article about one's body or garment; the ability to easily remove the garment following use; and the ability to refasten the garment multiple times, such as upon discovering that a diaper is clean following inspection.

However, prior art fastening systems have been deficient in various regards. For example, mechanical fastening systems used to secure disposable absorbent articles about a wearer are subjected to stressing forces during movement of the wearer. For example, hook and loop systems that secure diapers and training pants to a toddler are stressed as the toddlers crawl, run, jump, and otherwise move. These stressing forces can cause the hook components to pull away from the loop components, urging the hook components to disengage from the loop components. As prior art hook components are relatively rigid and non-extensible, and prior art loop fibers are relatively non-extensible, there exists little "play" in the connections between the hook and loop components. Consequently, the aforementioned stressing forces often result in the hook and loop components disengaging from each other, causing a garment to come loose from a wearer. Moreover, such stressing forces can cause what are often very thin loop fibers to break, rendering them unable to properly reengage hook components, such as upon an attempt to refasten a training pant or diaper about a wearer after inspection by a caregiver. A mechanical fastening system that overcomes these performance problems is lacking in the prior art. Furthermore, disposable absorbent articles that avoid these fastening issues are needed.

SUMMARY OF THE INVENTION

In response to the issues outlined above, a new mechanical fastening system has been invented. The new mechanical fastening system is particularly well suited for use in disposable absorbent articles.

In one aspect, the present invention relates to a mechanical fastening system that includes a male component and a female component. The male component includes a plurality of male engaging elements, and the female component includes a plurality of female engaging elements adapted for releasable direct engagement with the male engaging elements, wherein the female engaging elements comprise elastomeric fibers, and wherein the elastomeric fibers together define a fibrous web.

In another aspect, the present invention relates to a disposable absorbent article comprising a chassis that comprises a bodyside liner and a garment-side outer cover, and an absorbent assembly sandwiched between the liner and the outer cover. The disposable absorbent article further comprises a mechanical fastening system that includes a male component and a female component. The male component includes a plurality of male engaging elements, and the female component includes a plurality of female engaging elements adapted for releasable direct engagement with the male engaging elements, wherein the female engaging elements comprise elastomeric fibers, and wherein the elastomeric fibers together define a fibrous web.

The elastomeric loop material of certain aspects of the present invention can in particular embodiments provide benefits to the performance of a fastening system. For instance, as a mechanical fastening system is stressed in-use as discussed above, the elastomeric fibers stretch to provide a certain amount of "play" (i.e., freedom of movement) in the connection between the male and female components of the fastening system, enhancing the ability of the fastening system to remain fastening while under a limited amount of stress. Furthermore, in particular embodiments, an elastomeric loop fiber is more likely to remain engaged with a male fastening element until the male fastening element is rotated a substantial amount such the loop fiber can slide or "pop" off the male fastening element. This characteristic can be particularly useful in the context of disposable absorbent articles, as the elastomeric loop materials will remain engaged with the male engaging components during limited planar and rotational movement of the male fastening component (due to the ability of the elastomeric loop fibers to stretch and provide some "play" in the system), and disengage only when a significant amount of peel force and upward removal angle is applied to one or more fastening components in the system (such as during a caregiver's intentional effort to disengage the fastener for inspection or removal of the article).

BRIEF DESCRIPTION OF THE FIGURES

The above-mentioned and other features of the present invention, and the manner of obtaining them, will become more apparent and the invention itself will be better understood by reference to the following description of the embodiments of the invention taken in conjunction with the accompanying drawings, wherein:

FIG. 6A representatively illustrates a side view of one embodiment of the fastening system according to the present invention.

Corresponding reference characters indicate corresponding parts throughout the drawings.

DEFINITIONS

Figure 1:
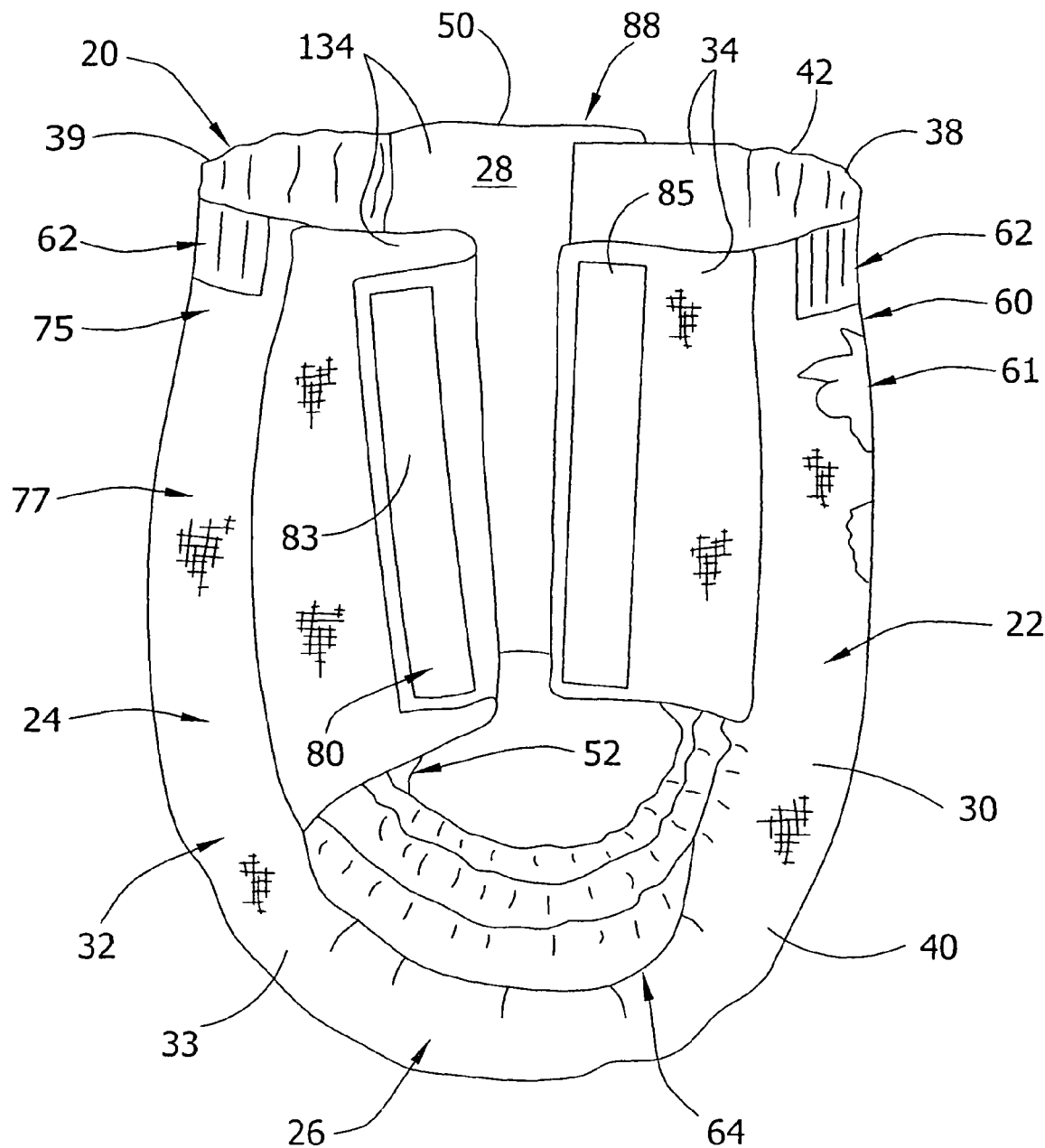
FIG. 1 representatively illustrates an absorbent article according to one aspect of the present invention in the form of a child's training pant, where the fastening system is shown engaged on one side of the training pant and disengaged on the other side of the training pant.

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Extensible" refers to a material or composite that is stretchable or capable of being elongated in at least one direction, but which may not have sufficient recovery to be considered elastic.

"Fabrics" is used to refer to all of the woven, knitted and nonwoven fibrous webs.

"Flexible" refers to materials which are compliant and which will readily conform to the general shape and contours of the wearer's body.

"Force" includes a physical influence exerted by one body on another which produces acceleration of bodies that are free to move and deformation of bodies that are not free to move.

"Graphic" refers to any design, pattern, or the like that is visible on an absorbent article.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, while fibers having contact angles greater than 90 degrees are designated "nonwettable" or hydrophobic.

"Integral" is used to refer to various portions of a single unitary element rather than separate structures bonded to or placed with or placed near one another.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Liquid impermeable", when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

Figure 2:
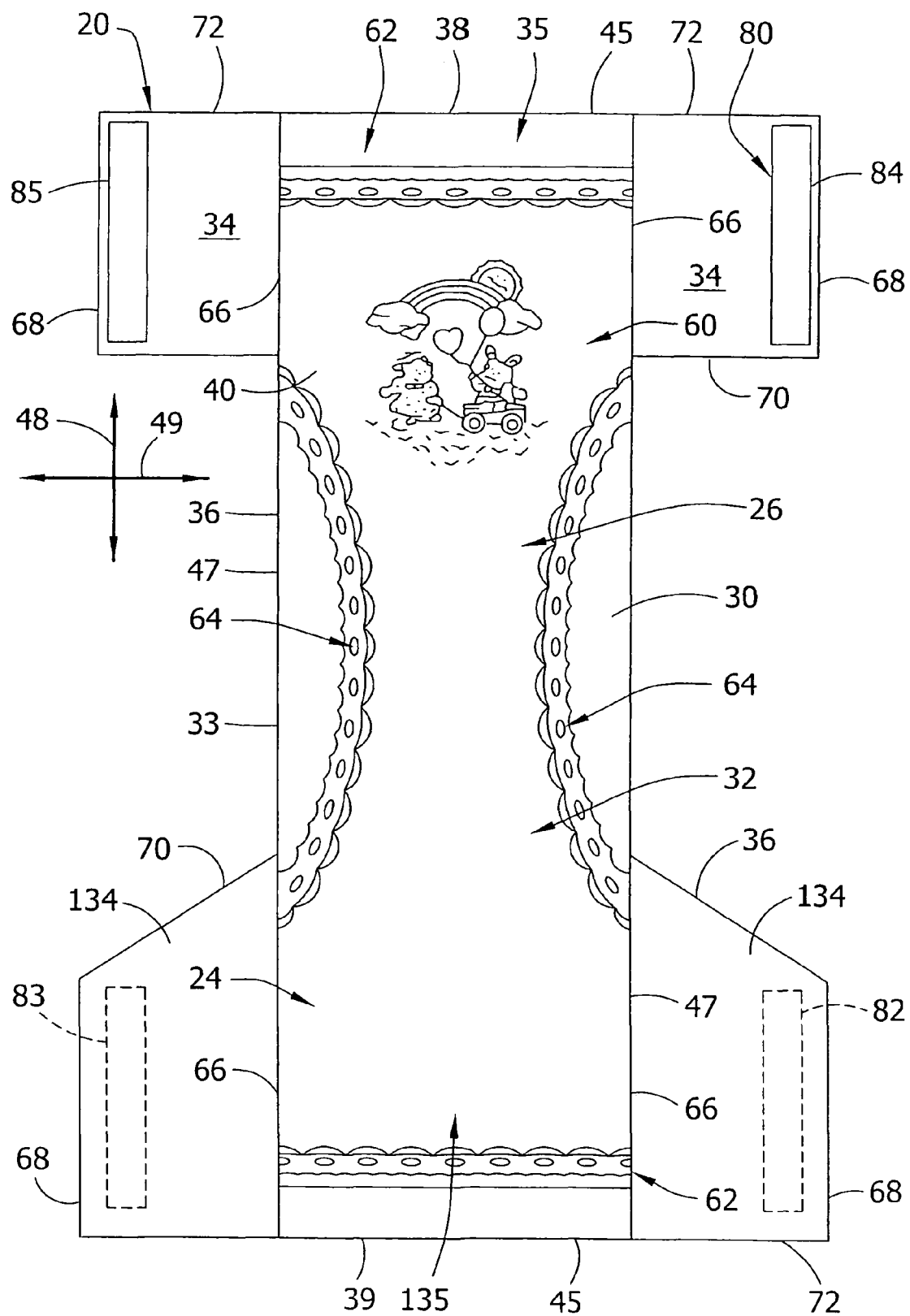
FIG. 2 representatively illustrates a plan view of the training pant shown in FIG. 1 in an unfastened, stretched and laid flat condition, and showing the surface of the training pant that faces away from the wearer.
Figure 3:
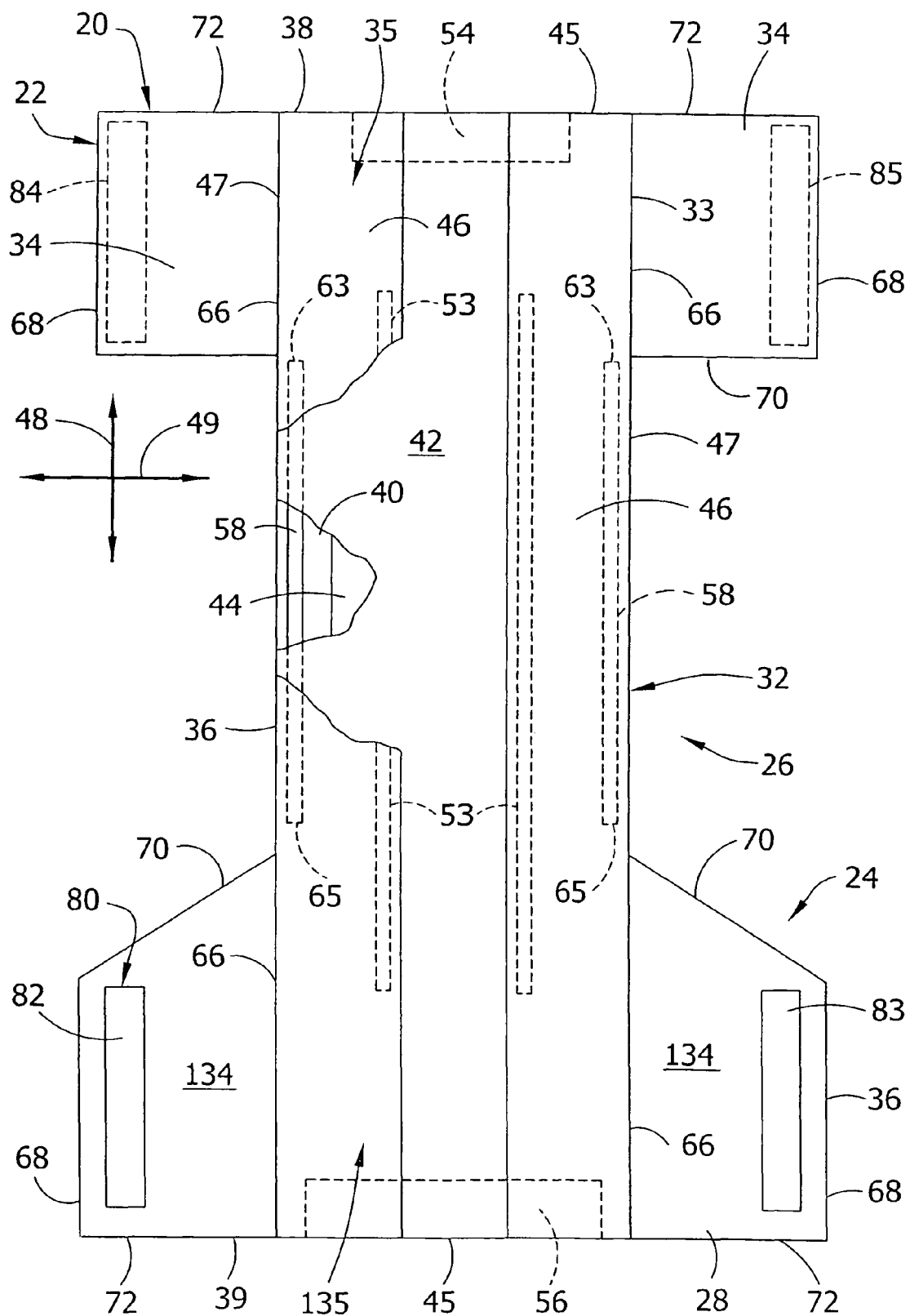
FIG. 3 representatively illustrates a plan view similar to FIG. 2, but showing the surface of the training pant that faces the wearer when the training pant is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," with reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Outer cover graphic" refers to a graphic that is directly visible upon inspection of the exterior surface of a garment, and for a refastenable garment is in reference to inspection of the exterior surface of the garment when the fastening system is engaged as it would be during use.

"Permanently bonded" refers to the joining, adhering, connecting, attaching, or the like, of two elements of an absorbent garment such that the elements tend to be and remain bonded during normal use conditions of the absorbent garment.

"Refastenable" refers to the property of two elements being capable of attachment, separation, and subsequent reattachment.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Stretch bonded" refers to an elastic member being bonded to another member while the elastic member is extended at least about 25 percent of its relaxed length. Desirably, the term "stretch bonded" refers to the situation wherein the elastic member is extended at least about 100 percent, and more desirably at least about 300-600 percent, of its relaxed length when it is bonded to the other member.

"Stretch bonded laminate" refers to a composite material having at least two layers in which one layer is a gatherable layer and the other layer is an elastic layer. The layers are joined together when the elastic layer is in an extended condition so that upon relaxing the layers, the gatherable layer is gathered.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DESCRIPTION OF PARTICULAR EMBODIMENTS

The present invention relates in one aspect to disposable articles, such as disposable absorbent articles, which employ a new fastening system. Examples of disposable articles within the scope of the present invention include diapers, training pants, incontinence garments, feminine care pads, disposable relatively non-absorbent clothing, and the like. For purposes of illustration, the disposable-article aspect of the invention shall now be described in the context of a child's training pant, representative embodiments of which are illustrated in FIGS. 1-5.

FIG. 1 representatively illustrates one embodiment of training pant 20 in accordance with the present invention in a partially fastened condition. The training pant 20 comprises an absorbent body 32 and a fastening system 80. The absorbent body 32 defines a front waist region 22, a back waist region 24, a crotch region 26 interconnecting the front and back waist regions, an inner surface 28 which is configured to contact the wearer, and an outer surface 30 opposite the inner surface which is configured to contact the wearer's clothing. With additional reference to FIGS. 2 and 3, the absorbent body 32 also defines a pair of transversely opposed side edges 36 and a pair of longitudinally opposed waist edges, which are designated front waist edge 38 and back waist edge 39. The front waist region 22 is contiguous with the front waist edge 38, and the back waist region 24 is contiguous with the back waist edge 39.

The illustrated absorbent body 32 comprises a rectangular composite structure 33, a pair of transversely opposed front side panels 34, and a pair of transversely opposed back side panels 134. The composite structure 33 and side panels 34 and 134 may be integrally formed or comprise two or more separate elements, as shown in FIG. 1. The illustrated composite structure 33 comprises an outer cover 40, a body side liner 42 (FIG. 3) which is connected to the outer cover in a superposed relation, an absorbent assembly 44 (FIG. 3) which is located between the outer cover and the body side liner, and a pair of containment flaps 46 (FIG. 3). The illustrated composite structure 33 has opposite linear end edges 45 that form portions of the front and back waist edges 38 and 39, and opposite linear side edges 47 that form portions of the side edges 36 of the absorbent body 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back waist regions 22 and 24 are joined together to define a three-dimensional pant configuration having a waist opening 50 and a pair of leg openings 52. The front waist region 22 comprises the portion of the training pant 20 which, when worn, is positioned on the front of the wearer while the back waist region 24 comprises the portion of the training pant which, when worn, is positioned on the back of the wearer. The crotch region 26 of the training pant 20 comprises the portion of the training pant which, when worn, is positioned between the legs of the wearer and covers the lower torso of the wearer. The front and back side panels 34 and 134 comprise the portions of the training pant 20 which, when worn, are positioned on the hips of the wearer.

The front waist region 22 of the absorbent body 32 includes the transversely opposed front side panels 34 and a front center panel 35 (FIGS. 2 and 3) positioned between and interconnecting the side panels. The back waist region 24 of the absorbent body 32 includes the transversely opposed back side panels 134 and a back center panel 135 (FIGS. 2 and 3) positioned between and interconnecting the side panels. The waist edges 38 and 39 of the absorbent body 32 are configured to encircle the waist of the wearer when worn and provide the waist opening 50 which defines a waist perimeter dimension. Portions of the transversely opposed side edges 36 in the crotch region 26 generally define the leg openings 52. The waist regions 22 and 24 jointly define a waistband 75 (FIGS. 1 and 4) that peripherally surrounds the waist opening 50 of the pant 20. The waist regions 22 and 24 also jointly define a hip section 77 (FIGS. 1 and 4) that encircles the pant 20 and is disposed between the waistband 75 and the leg openings 52.

The absorbent body 32 is configured to contain and/or absorb any body exudates discharged from the wearer. For example, the absorbent body 32 desirably although not necessarily comprises the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright configuration in at least the crotch region 26 of the training pant 20 to form a seal against the wearer's body. The containment flaps 46 can be located along the transversely opposed side edges of the absorbent body 32, and can extend longitudinally along the entire length of the absorbent body or may only extend partially along the length of the absorbent body. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably although not necessarily includes a front waist elastic member 54, a rear waist elastic member 56, and leg elastic members 58, as are known to those skilled in the art (FIG. 3). The waist elastic members 54 and 56 can be operatively joined to the outer cover 40 and/or body side liner 42 along the opposite waist edges 38 and 39, and can extend over part or all of the waist edges, such that the waist elastic members are disposed in the waistband 75 in the fully assembled pant.

The leg elastic members 58 are desirably operatively joined to the outer cover 40 and/or body side liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 comprise a plurality of dry-spun coalesced multifilament spandex elastomeric threads sold under the trade name LYCRA and available from Invista, Wichita, Kan., U.S.A.

In particular embodiments, the waist elastic members 54 and 56 can be formed of retractive materials. For example, the waist elastic members 54 and 56 can be formed of an elastomeric material that is adapted to retract upon activation by a source of heat such as disclosed in U.S. Pat. No. 4,640,726.

The outer cover 40 desirably comprises a material that is substantially liquid impermeable, and can be elastic or inelastic. The outer cover 40 can be a single layer of liquid impermeable material, but desirably comprises a multi-layered laminate structure in which at least one of the layers is liquid impermeable. For instance, the outer cover 40 can include a liquid permeable outer layer and a liquid impermeable inner layer that are suitably joined together by laminate adhesive, ultrasonic bonds, thermal bonds, or the like. Suitable laminate adhesives, which can be applied continuously or intermittently as beads, a spray, parallel swirls, or the like, can be obtained from Findley Adhesives, Inc., of Wauwatosa, Wis. U.S.A., or from National Starch and Chemical Company, Bridgewater, N.J. U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of an elastomeric material as provided by this invention, constituting an integral and functional loop material covering the entire outer surface of the cover 40. While it is not a necessity for outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Huntsman Packaging of Newport News, Va. U.S.A. If the outer cover 40 is a single layer of material, it can be embossed and/or matte finished providing a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. U.S.A.

As shown in FIGS. 1 and 2, the training pant 20 and in particular the outer cover 40 desirably comprises one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated fly openings for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated training pant 20, which is designed for use by young girls, includes a registered outer cover graphic 60. In this design, the registered graphic 60 includes a primary pictorial image 61, simulated waist ruffles 62, and simulated leg ruffles 64. The primary pictorial image 61 includes a rainbow, sun, clouds, animal characters, wagon and balloons. Any suitable design can be utilized for a training pant intended for use by young girls, so as to be aesthetically and/or functionally pleasing to them and the caregiver. The appearance-related components are desirably positioned on the training pant 20 at selected locations, which can be carried out using the methods disclosed in U.S. Pat. No. 5,766,389 issued Jun. 16, 1998 to Brandon et al., which is incorporated herein by reference. The primary pictorial image 61 is desirably positioned in the front waist region 22 along the longitudinal centerline of the training pant 20.

The liquid permeable body side liner 42 is illustrated as overlying the outer cover 40 and absorbent assembly 44, and may but need not have the same dimensions as the outer cover 40. The body side liner 42 is desirably compliant, soft feeling, and non-irritating to the child's skin. Further, the body side liner 42 can be less hydrophilic than the absorbent assembly 44, to present a relatively dry surface to the wearer and permit liquid to readily penetrate through its thickness. Alternatively, the body side liner 42 can be more hydrophilic or can have essentially the same affinity for moisture as the absorbent assembly 44 to present a relatively wet surface to the wearer to increase the sensation of being wet. This wet sensation can be useful as a training aid. The hydrophilic/hydrophobic properties can be varied across the length, width and depth of the body side liner 42 and absorbent assembly 44 to achieve the desired wetness sensation or leakage performance.

The body side liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 42. For example, the body side liner can be composed of a meltblown or spunbonded web of polyolefin fibers. The body side liner can also be a bonded-carded web composed of natural and/or synthetic fibers. The body side liner can also be made of an elastomeric material as provided by this invention, constituting an integral and functional loop material covering the entire surface of the body side liner 42. The body side liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture comprising Ahcovel N-62 from Hodgson Textile Chemicals of Mount Holly, N.C. U.S.A. and Glucopan 220UP from Henkel Corporation of Ambler, Pa. in an active ratio of 3:1. The surfactant can be applied by any conventional means, such as spraying, printing, brush coating or the like. The surfactant can be applied to the entire body side liner 42 or can be selectively applied to particular sections of the body side liner, such as the medial section along the longitudinal centerline.

A suitable liquid permeable body side liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like.

The absorbent assembly 44 (FIG. 3) is positioned between the outer cover 40 and the body side liner 42, which components can be joined together by any suitable means such as adhesives, ultrasonic bonds, thermal bonds, or the like. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably comprise a matrix of hydrophilic fibers, such as a web of cellulose fluff, mixed with particles of a high-absorbency material commonly known as superabsorbent material. In a particular embodiment, the absorbent assembly 44 comprises a matrix of cellulosic fluff, such as wood pulp fluff, and superabsorbent hydrogel-forming particles. The wood pulp fluff can be exchanged with synthetic, polymeric, meltblown fibers or short cut homofilament or bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich. U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and comprises a blend of wood pulp fluff and superabsorbent material. One preferred type of pulp is identified with the trade designation CR1654, available from U.S. Alliance, Childersburg, Ala. U.S.A., and is a bleached, highly absorbent sulfate wood pulp containing primarily soft wood fibers and about 16 percent hardwood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that may help maintain the integrity and/or shape of the absorbent assembly.

The absorbent body 32 can also incorporate other materials that are designed primarily to receive, temporarily store, and/or transport liquid along the mutually facing surface with absorbent assembly 44, thereby maximizing the absorbent capacity of the absorbent assembly. One suitable material is referred to as a surge layer (not shown) and comprises a material having a basis weight of about 50 to about 120 grams per square meter, and comprising a through-air-bonded-carded web of a homogenous blend of 60 percent 3 denier type T-256 bicomponent fiber comprising a polyester core/polyethylene sheath and 40 percent 6 denier type T-295 polyester fiber, both commercially available from Kosa Corporation of Salisbury, N.C. U.S.A.

As noted previously, the illustrated training pant 20 has front and back side panels 34 and 134 disposed on each side of the absorbent body 32. These transversely opposed front side panels 34 and transversely opposed back side panels 134 can be permanently bonded along attachment lines 66 to the composite structure 33 of the absorbent body 32 in the respective front and back waist regions 22 and 24. More particularly, as shown best in FIGS. 2 and 3, the front side panels 34 can be permanently bonded to and extend transversely beyond the linear side edges 47 of the composite structure 33 in the front waist region 22, and the back side panels 134 can be permanently bonded to and extend transversely beyond the linear side edges of the composite structure in the back waist region 24. The side panels 34 and 134 may be attached using attachment means known to those skilled in the art such as adhesive, thermal or ultrasonic bonding. Alternatively, the side panels 34 and 134 can be formed as a portion of a component of the composite structure 33. For example, the side panels can comprise a generally wider portion of the outer cover, the body side liner, and/or another component of the absorbent body.

The side panels 34 and 134 preferably but not necessarily have elastic properties with sufficient extensibility to allow the wearer to pull the product up without having to open the fasteners on the pant. The side panels 34 and 134 also preferably provide sufficient retraction tension at extensions normally seen during wear to ensure good fit during wear without adjusting the fastener position. If the outer cover 40, as described above, comprises an elastic material, the side panels 34 and 134 may require less extensibility. Alternatively, the pant may have an all-over stretch material across the entire width of the pant, comprising the outer cover 40 and side panels 34 and 134 as a single material component. The extension requirements of the side panels 34 and 134 are determined by the desired fit range for the product and the interaction with extension of other components, e.g., outer cover 40.

The illustrated side panels 34 and 134 each define a distal edge 68 that is spaced from the attachment line 66, a leg end edge 70 disposed toward the longitudinal center of the training pant 20, and a waist end edge 72 disposed toward a longitudinal end of the training pant. The leg end edge 70 and waist end edge 72 extend from the side edges 47 of the composite structure 33 to the distal edges 68. The leg end edges 70 of the side panels 34 and 134 form part of the side edges 36 of the absorbent body 32. In the back waist region 24, the leg end edges 70 are desirably although not necessarily curved and/or angled relative to the transverse axis 49 to provide greater coverage toward the back of the pant as compared to the front of the pant. The waist end edges 72 are desirably parallel to the transverse axis 49. The waist end edges 72 of the front side panels 34 form part of the front waist edge 38 of the absorbent body 32, and the waist end edges 72 of the back side panels 134 form part of the back waist edge 39 of the absorbent body.

In particular embodiments for improved fit and appearance, the side panels 34 and 134 desirably have an average length dimension measured parallel to the longitudinal axis 48 that is about 15 percent or greater, and particularly about 20 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, or can include a single piece of material which is folded over upon itself (not shown). The side panels 34 and 134 desirably although not necessarily comprise an elastic material capable of stretching in a direction generally parallel to the transverse axis 49 of the training pant 20. Suitable elastic materials, as well as one process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material comprises a stretch-thermal laminate, a neck-bonded laminate, a reversibly necked laminate, or a stretch-bonded laminate material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may comprise other woven or nonwoven materials, such as those described above as being suitable for the outer cover 40 or body side liner 42; mechanically prestrained materials; or extensible but inelastic materials. In particular embodiments, one or more of the side panels 34 and 134 can be formed of retractive materials. For example, the side panels 34 and 134 can be formed of an elastomeric material that is adapted to retract upon activation by a source of heat, such as disclosed in U.S. Pat. No. 4,640,726.

The illustrated training pant 20 includes a fastening system 80 for refastenably securing the training pant about the waist of the wearer. The illustrated fastening system 80 includes first fastening components 82 and 83 that are adapted to refastenably connect to mating second fastening components 84 and 85. In one embodiment representatively illustrated in FIG. 6, one surface of each of the first fastening components 82 and 83 comprises a plurality of engaging elements 182 that project from that surface. The engaging elements of the first fastening components 82 and 83 are adapted to repeatedly engage and disengage engaging elements 184 of the second fastening components 84 and 85.

The first fastening components 82 and 83, alternatively referred to as the male component or the hook or hook-type component, can have any configuration which will allow them to properly engage the second fastening components 84 and 85, alternatively referred to as the female component or the loop or loop-type component. The male component in particular embodiments comprises a material having a base or backing structure 86 (FIG. 6) and a plurality of hook members 182 extending upwardly from at least one surface of the backing structure 86. The hook material 82 advantageously comprises a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82-85 are available from commercial vendors such as Velcro Industries B.V., Amsterdam, Netherlands or affiliates thereof, and are identified as Velcro HTH-829 with a unidirectional hook pattern and having a thickness of about 0.9 millimeters (35 mils) and HTH-851 with a unidirectional hook pattern and having a thickness of about 0.5 millimeters (20 mils); and Minnesota Mining & Manufacturing Co., St. Paul, Minn. U.S.A., including specific materials identified as CS-600. Additional examples of hook materials suitable for use in conjunction with the fastening system of the present invention are disclosed in U.S. Pat. No. 4,984,399 to Provost et al. and U.S. Pat. No. 5,339,499 to Kennedy et al.

In alternative embodiments contemplated by this invention, fasteners 82-85 can be located anywhere over the front or back regions 22 and 24 of the pant. The fasteners 82-85 can be integral to any of the materials on the pant in the front or back regions 22 and 24. The fasteners can be integral to the entire outer cover of the pant (e.g. in a one piece outer cover product) or integral to the entire liner in the pant. The fasteners can be integral to panels 34 and/or 134. Alternatively, any of the fasteners 82-85 can be affixed to an underlying layer, and such underlying layer can be elastomeric, merely stretchable, or non-extensible.

With particular reference to FIG. 3, the first fastening components 82 and 83 are desirably although not necessarily disposed on the inner surface 28 of the training pant 20 in the back waist region 24. The first fastening components 82 and 83 are desirably positioned along the distal edges 68 of the back side panels 134, and abutting or adjacent to the waist end edge 72. In certain embodiments, for example, the first fastening components 82 and 83 can be located within about 2 centimeters, and more particularly within about 1 centimeter, of the distal edges 68, the waist end edges 72, and the leg end edges 70.

With particular reference to FIG. 2, the second fastening components 84 and 85 are desirably although not necessarily disposed on the outer surface 30 of the training pant 20 in the front waist region 22. The second fastening components 84 and 85 are sized to receive the first fastening components 82 and 83 and are desirably positioned along the distal edges 68 of the front side panels 34, and abutting or adjacent to the waist end edge 72. In certain embodiments, for example, the second fastening components 84 and 85 can be located within about 2 centimeters, and more particularly within about 1 centimeter, of the distal edges 68, the waist end edges 72, and the leg end edges 70. Where the first fastening components 82 and 83 comprise loop type fasteners disposed on the inner surface 28 and the second fastening components 84 and 85 comprise hook type fasteners disposed on the outer surface 30, the first fastening components can be sized larger than the second fastening components to ensure coverage of the rigid, outwardly-directed hooks. The loop fastening components can be integral with the side panels or adhered to the side panels 34 and 134 by any means known to those skilled in the art such as adhesive bonds, sonic bonds or thermal bonds. The loop fastening components can be extensible and bonded in overlaying relationship onto any layer of the body 32 in a manner that retains the extension and retraction characteristics of the loop fastening components.

The fastening components are desirably rectangular, although they may alternatively be square, round, oval, curved or otherwise non-rectangular in shape. In particular embodiments, each of the fastening components 82-85 defines a length dimension aligned generally parallel with the longitudinal axis 48 of the training pant 20 and a width dimension aligned generally parallel with the transverse axis 49 of the training pant. For a child of about 9 to about 15 kilograms (20-33 pounds), for example, the length dimension of the fastening components is desirably from about 5 to about 13 centimeters, such as about 8 centimeters, and the width dimension is desirably from about 0.5 to about 3 centimeters, such as about 1 centimeter. With particular embodiments, the fastening components can have a length-to-width ratio of about 2 or greater, such as about 2 to about 25, and particularly about 5 or greater, such as about 5 to about 8. For other embodiments such as for adult products, it may be desirable for one or more of the fastening components to comprise a plurality of relatively smaller fastening elements. In that case, a fastening component or individual fastening elements may have an even smaller length-to-width ratio, for example, of about 2 or less, and even about 1 or less.

When the fastening components 82-85 are releasably engaged, the side edges 36 of the absorbent body 32 in the crotch region 26 define the leg openings 52, the waist edges 38 and 39 of the absorbent body, including the waist end edges 72 of the side panels, define the waist opening 50, and the waist regions 22 and 24 jointly define a waistband 75 and hip section 77. For improved formation of the leg openings 52, it can be desirable in some embodiments for the front side panels 34 to be longitudinally spaced from the back side panels 134 (see FIGS. 2 and 3). For example, the front side panels 34 can be longitudinally spaced from the back side panels 134 by a distance equal to about 20 percent or greater, particularly from about 20 to about 60 percent, and more particularly from about 35 to about 50 percent, of the overall length dimension of the absorbent article.

When connected, the fastening components 82-85 form refastenable seams 88 (FIG. 1) that desirably although not necessarily extend substantially the entire distance between the waist opening 50 and the leg openings 52. More specifically, the refastenable seams 88 can cover about 80 to 100 percent, and particularly about 90 to about 98 percent, of the distance between the waist opening 50 and each leg opening 52, which distance is measured parallel to the longitudinal axis 48. To construct the seams 88 to extend substantially the entire distance between the waist and leg openings 50 and 52, the fastening components 82-85 can be formed to cover about 80 to 100 percent, and more particularly about 90 to about 98 percent, of the distance between the waist end edge 70 and the leg end edge 72 of the side panels 34 and 134. In other embodiments, the fastening components can comprise a plurality of smaller fastening elements covering a smaller portion of the distance between the waist opening 50 and the leg openings 52, for example, about 20 to about 70 percent, but spaced apart to span a larger percentage of the distance between the waist opening and the leg openings.

It is also contemplated that the fastening components 82-85 may be incorporated as integral portions of the pant rather than separate components applied during manufacture. If the fastening components 82 and 83, are a single component and are integral to the pant in the front region 22, for example, the size and the shape of the fastening component is directly equal to the size and shape of that region. If the fastening components 82-85 are integral parts of side panels 34 and/or 134, for another example, the fastening components are the same size and shape as the side panels 34 and/or 134.

For the refastenable seams 88 to be located at the sides of the wearer, it can be particularly desirable for the transverse distance between the first fastening components 82 and 83 to be substantially equal to the transverse distance between the second fastening components 84 and 85. The transverse distance between a set of fasteners is the distance measured parallel to the transverse axis 49 between the longitudinal centerlines of the fasteners, measured with the side panels 34 and 134 in their relaxed, or non-extended, condition. In an alternative embodiment, the training pant 20 includes only a single second fastening component disposed in the front waist region 22 for refastenably connecting the first fastening components 82 and 83 (not shown).

Figure 4:
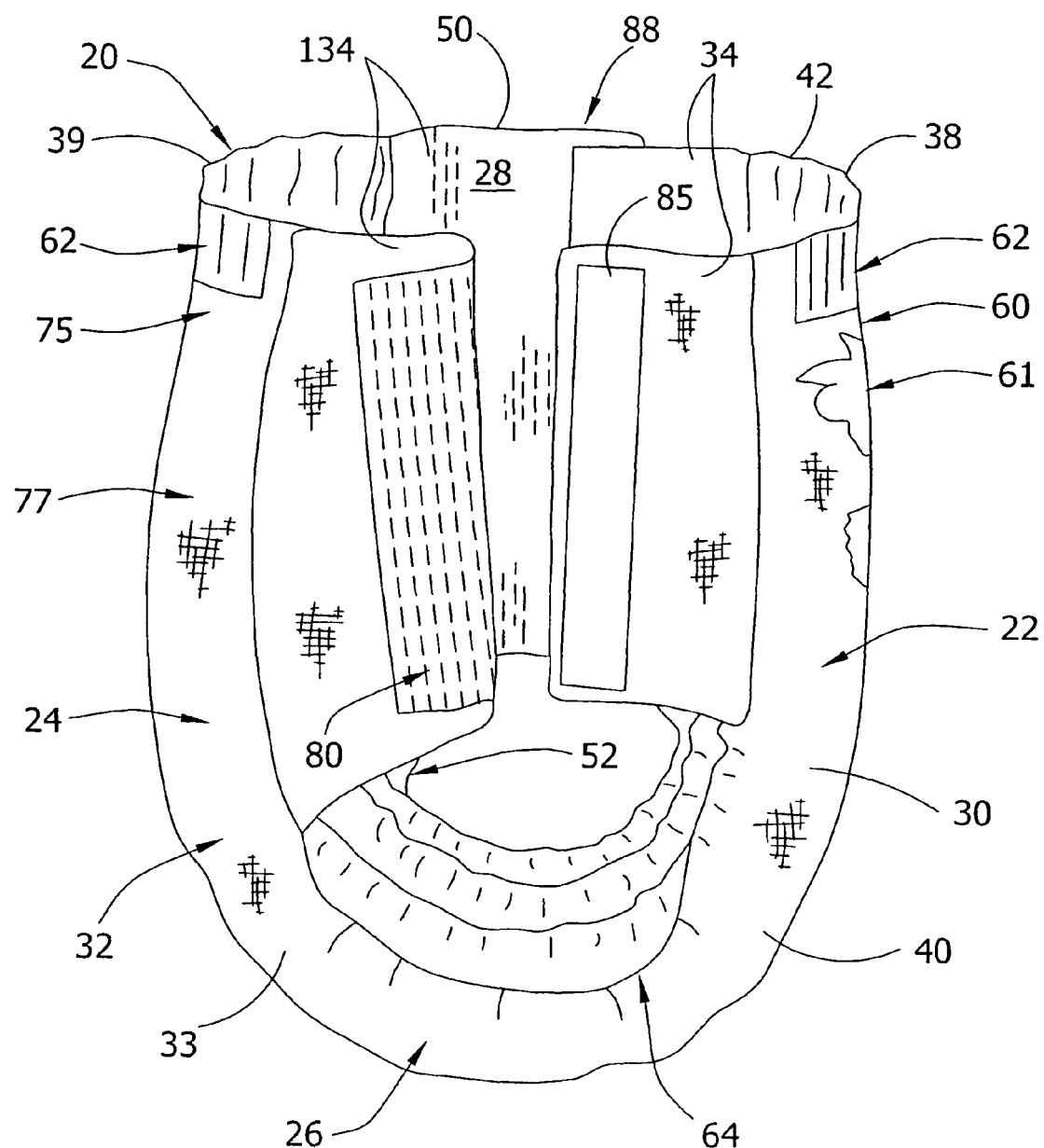
FIG. 4 representatively illustrates an alternative embodiment of the present invention in a side perspective view similar to FIG. 1.
Figure 5:
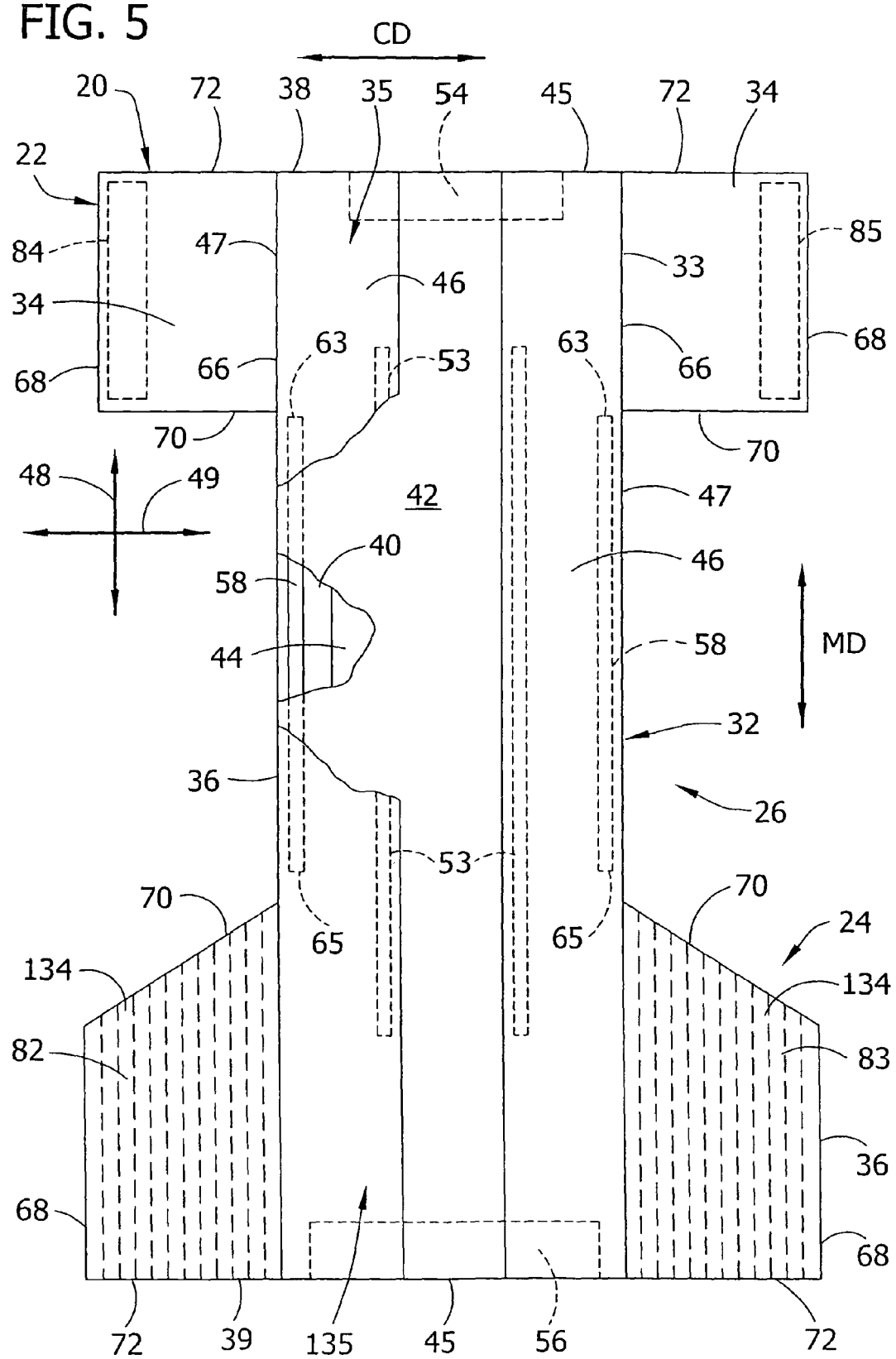
FIG. 5 representatively illustrates a plan view of the embodiment of FIG. 4 in a similar position as FIG. 3.

In a further alternative embodiment illustrated in FIGS. 4 and 5, one or both of the fastening components can comprise integral portions of the waist regions. For instance, the front and back side panels 34 and 134 can function as fastening components in that they can comprise a material that is releasably engageable with complementary fastening components disposed in the opposite waist region. As illustrated in FIGS. 4 and 5, the side panels 134 are made completely of an elastomeric loop material in accordance with the present invention. Alternatively, these side panels could be made of elastomeric loop material only at their outer edges where they will engage the hook material, and the remainder of the side panels can be made of some other, preferably extensible, material and joined along abutting edges thereof.

In particular embodiments of the present invention, the first fastening components 82 and 83 each comprise hook or mushroom-type fasteners and the second fastening components 84 and 85 each comprise complementary fasteners formed of elastomeric nonwoven loop material. In another embodiment, the first fastening components 82 and 83 each comprise fasteners formed of elastomeric loop material and the second fastening components 84 and 85 each comprise complementary hook type fasteners. Although the illustrated embodiments show the back waist region 24 overlapping the front waist region 22, which is convenient, the training pant 20 can also be configured so that the front waist region overlaps the back waist region.

Figure 6:
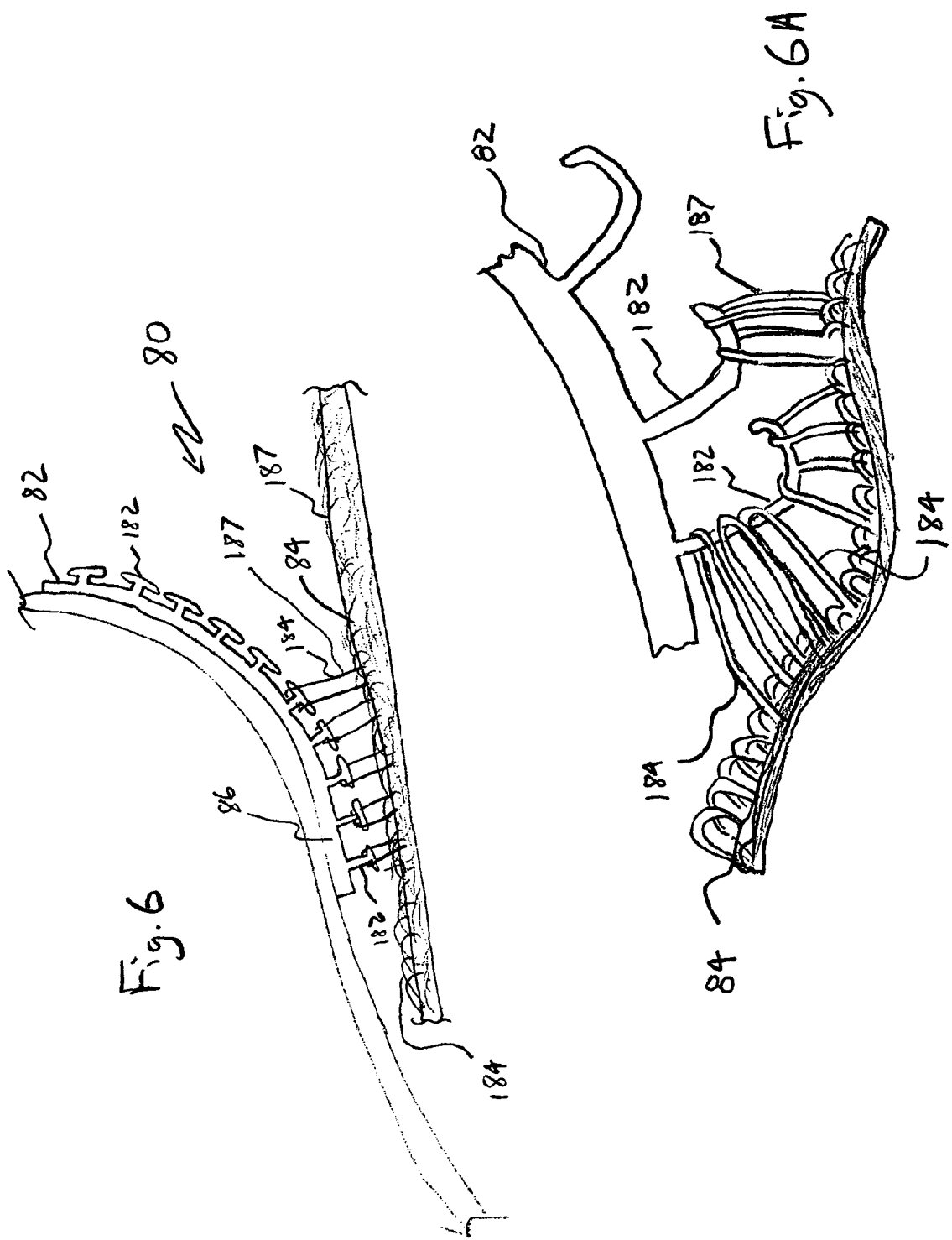
FIG. 6 representatively illustrates a side view of one embodiment of the fastening system according to one aspect of the present invention.

Referring to FIG. 6, the loop-type fastener, such as the second fastening component 84, preferably comprises elastomeric fibers 187. In particular embodiments, the loop fastener comprises a nonwoven web of substantially continuous elastomeric fibers. The loop-type fastener 84 includes a plurality of engaging elements 184 in the form of elastomeric fibers adapted to directly engage a plurality of engaging elements 182 of the hook-type fastener 82. In particular embodiments, the elastomeric loop material comprises a plurality of engaging elements 184 in the form of elastomeric fibers 187 attached to an elastic substrate (not shown) to generate an elastomeric composite that provides retraction tension over a suitable range of extensions. In particular embodiments of the invention, representatively illustrated in FIG. 6A, individual hook-type engaging elements 182 each engage two or more loop-type engaging elements 184. It is believed that, in certain embodiments, the elastomeric nature of the fibers constituting the loop-type engaging elements 182 of the present invention stretch when pulled on by hook-type fastening components 184 (such as during fastening or during donning of a prefastened, refastenable garment), and that such stretching allows several loop-type engaging elements to engage a single hook-type engaging element 182. It is believed that such "multiple looping" can create a more secure, robust connection within a fastening system, and that individual loop fibers are less likely to break when stressed.

The elastomeric loop material 84 of certain aspects of the present invention comprises elastomeric fibers 187 that can be made in accordance with the teachings of U.S. Patent Application Publication 2004/0110442 to Rhim et al., incorporated herein by reference thereto. Alternatively, the elastomeric fibers can be made in accordance with the teachings of U.S. Pat. Nos. 5,470,639 and 5,997,989, both to Gessner et al. and incorporated herein by reference thereto. The elastomeric fibers 187 suitable for use in the elastomeric loop may be formed by known nonwoven processes, such as, for example, meltblowing processes or spunbonding processes. The elastomeric loop can in particular embodiments be any material with a network of substantially continuous fibers or filaments that can be stretched upon application of a force in one direction without material failure, i.e., breaking or tearing.

The elastomeric loop fibers 187 can comprise a polymeric material. In one particular embodiment, for example, the elastomeric loop fibers comprise a plurality of dry-spun coalesced multifilament spandex elastomeric threads sold under the trade name LYCRA and available from Invista, Wichita, Kan., U.S.A. In another example, the elastomeric loop fibers comprise materials that can be spun or otherwise formed into a continuous fiber. In particular embodiments, the loop fiber must be capable of being stretched and have a high recovery percentage. Suitable elastomeric materials that can comprise at least a part of an elastomeric loop fiber include melt extrudable thermoplastic elastomers such as a polyurethane elastomer, a copolyether ester, a polyether block polyamide copolymer, an ethylene vinyl acetate (EVA) elastomer, a styrenic block copolymer, an olefinic elastomer or plastomer, as well as other elastomers known to those skilled in the polymer art. Particularly suitable elastomers include styrenic block copolymers such as those available from KRATON® Polymers. KRATON® is a registered trademark of Kraton Polymers having an office in Houston, Tex.

In particular embodiments, the elastomeric loop fibers 187 of the present invention comprise bicomponent fibers. The term "bicomponent fibers" refers to fibers which have been formed from at least two polymer sources extruded from separate extruders but spun together to form one fiber. Bicomponent fibers are also sometimes referred to as conjugate fibers or multicomponent fibers. The polymers are arranged in substantially constantly-positioned distinct zones across the cross-sections of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement. Bicomponent fibers are taught by U.S. Pat. No. 5,108,820 to Kaneko et al., U.S. Pat. No. 4,795,668 to Krueger et al., U.S. Pat. No. 5,540,992 to Marcher et al., and U.S. Pat. No. 5,336,552 to Strack et al., and U.S. Pat. No. 5,425,987 to Shawver, each being incorporated by reference in its entirety. Bicomponent fibers are also taught by U.S. Pat. No. 5,382,400 to Pike et al. and by U.S. Pat. No. 6,225,243 to Austin, each being incorporated by reference in its entirety. For two component fibers, the polymers may be present in ratios of 75/25, 50/50, 25/75 or any other desired ratio. Additionally, polymer additives such as processing aids, may be included in each zone.

In particular embodiments, in which the elastomeric loops fibers are desired to be highly extensible and retractable via elasticized sheath/core bicomponent fibers, the ratio of the first component elastomer to the second component thermoplastic polymer need be relatively high, particularly in the sheath/core configuration. For instance, it is desirable to have at least between 70 and 98 percent core elastomer component (by weight) in such a material. Alternatively, it is desirable to have at least between 70 and 90 percent core elastomer component (by weight) in such a material. By uniformly distributing the minute amount of the second component without altering its rheological property, bicomponent fibers with the desired properties are achievable.

The first, elastomeric component in a bicomponent fiber is a material that can be spun or otherwise formed into a continuous fiber. In particular embodiments, elastomeric fiber must be capable of being stretched and have a high recovery percentage. Suitable elastomeric materials that can be used for the elastomeric component in a bicomponent fiber include melt extrudable thermoplastic elastomers such as a polyurethane elastomer, a copolyether ester, a polyether block polyamide copolymer, an ethylene vinyl acetate (EVA) elastomer, a styrenic block copolymer, an olefinic elastomer or plastomer, as well as other elastomers known to those skilled in the polymer art. Particularly suitable elastomers include styrenic block copolymers such as those available from KRATON® Polymers. KRATON® is a registered trademark of Kraton Polymers having an office in Houston, Tex.

The second component in the bicomponent fiber is, like the elastomeric component, a material that can be spun or otherwise formed into a continuous fiber. Since the first component (elastomer) does not typically have sufficiently high melt strength to be spun at the high speed of the spunbond process, the second component should desirably have sufficiently high melt strength to reinforce the first component without breaking spinlines (fibers). In particular embodiments, the second component may be formed from a polyolefin such as polyethylene or polypropylene, a polyester, a polyether or a polyamide. Still other suitable polyolefinic materials that can be used for the second component include random copolymers, such as a random copolymer containing propylene and ethylene, or materials such as blends, including but not limited to polypropylene/polybutylene blends and copolymers. The second component can also be formed from a melt extrudable thermoplastic material that provides permanent deformation upon stretching, that is, demonstrates a permanent set. Such materials include, but are not limited to polyamides.

As elastomeric polymers are in many instances sticky or tacky, and since in certain embodiments of the present invention it is desirable that the elastomeric loop fibers not be sticky or tacky, the elastomeric loop fibers of the present invention can be sheath/core bicomponent fibers in which the core comprises an first elastomeric component, and the sheath comprises a second, substantially non-elastomeric component. Desirably, the sheath material can be selected so as to not demonstrate tackiness or stickiness to the touch and such that it can be extruded in a thin consistent layer so as to sufficiently cover an elastomeric material contained adjacent to or within the sheath material. By covering a rubbery or sticky material with such a second component, the sticky elastomeric component can be used to provide elasticity but with its "sticky" feel concealed. Depending on the particular second component utilized, the sheath component of a sheath/core bicomponent material may or may not demonstrate surface corrugations. For instance, it has been found that while the use of polypropylene, or its blend with 10% polybutylene copolymer, in the sheath may lead to corrugated surface topographies, the use of polyethylene in a sheath may lead to relatively smooth surfaces.

In other embodiments of the invention, it is desirable that the loop-type component exhibit some amount of frictional resistance to enhance the robustness of the fastening system. For example, certain fibrous webs constructed of elastomeric fibers define surface characteristics that increase the amount of frictional resistance exhibited by the webs. The Example below lists various loop-type components and their frictional properties. It is believed that, in certain embodiments, greater frictional resistance in a loop-type component provides a more secure connection of the fastening system of which it is a part during fastening, donning, wearing, and/or refastening of disposable absorbent articles.

In particular embodiments, the elastomeric loop fibers include kinks, curls, or crimps. The terms "kink" and "curl" refer to a structural formation in a fiber, in which part of an extruded fiber is bent so as to include a non-linear configuration, such as by passing over itself. The term "crimp" refers to a repeating curl within a fiber and includes helical formations, coils or curls along the fiber length.

Figure 7:
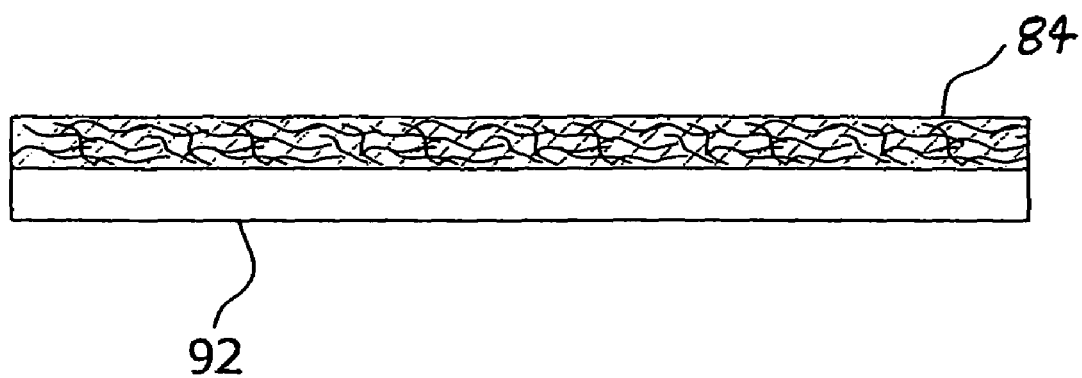
FIG. 7 representatively illustrates a side view of one embodiment of the elastomeric loop material affixed to a backing layer according to one aspect of the present invention.

The elastomeric material can be a multilayer material having, for example, at least one layer of elastomeric loop material joined to at least one layer of meltblown web, bonded carded web, polymeric film, or other suitable material. Also, as representatively illustrated in FIG. 7, the elastomeric loop component 84 can be attached to a base substrate 92, and the base substrate 92 could be elastomeric, merely stretchable, or non-extensible. It is believed that the elastic loop fibers can be attached to an inelastic base substrate and still provide some shock resistance to the fastening system during use due to the stretchability of the fibers and the resultant "play" introduced into the fastening system. However, in certain preferred embodiments, both the loop fibers and the base structure to which the loop fibers can be attached are stretchable or elastomeric. The elastomeric loop material may also be a composite material made of a mixture of two or more different fibers or a mixture of fibers and particulates.

If the elastomeric loop material is a nonwoven web of fibers, the fibers are ideally joined by interfiber bonding to form a coherent web structure which is able to withstand stretching forces. Interfiber bonding may be produced by entanglement between individual fibers. The fiber entangling may be generated by processes such as, for example, hydraulic entangling or needle punching. Alternatively and/or additionally, a bonding agent may be used to increase the desired bonding.

In particular embodiments, a nonwoven web which comprises the elastomeric loop material according to the present invention has a basis weight of at least about 0.3 ounces per square yard, more particularly at least about 0.4 ounces per square yard, and still more particularly at least about 0.5 ounces per square yard. In particular embodiments, a nonwoven web which comprises the elastomeric loop material according to the present invention has a basis weight of at most about 3.0 ounces per square yard, more particularly at most about 2.0 ounces per square yard, and still more particularly at most about 1.5 ounces per square yard.

It is also contemplated that when the training pants or the like garment are being initially constructed and folded by machine, the elastomeric loop material and/or its underlying support material of the various embodiments can be positioned over the hook material and then pressed thereon to give an initial construction that is more robust and less prone to intentional disengagement in the mechanical fastening system than conventional mechanical fastening systems.

EXAMPLES

As described above, it is believed that, in particular embodiments, loop-type components exhibiting a relatively high frictional resistance provide certain advantages in fastening systems used in disposable absorbent articles. To quantify this property in relation to certain aspects of the present invention, several loop-type materials were examined for frictional resistance. In particular, the kinetic coefficients of friction between various loop-type materials and two particular surfaces were measured. To estimate the surface-to-surface frictional forces that exist between male engaging elements and female engaging elements when a fastening system is fastened, the loop-type materials were rubbed in one instance against a Plexiglas®-type plate, and in another instance against the smooth back side of a hook component (the smooth side having no engaging elements projecting therefrom). The back side of the hook component was used so that the loop-type component could freely slide along the tactile surface of the hook component, without becoming bound up by the engaging elements.

The kinetic coefficients of friction were determined using the Test Procedure described below. The results are displayed in the Table below. Each material sample measured 67 mm by 152 millimeters, and was tested with a modified version of the ASTM D 1894-00 procedure referenced in the Test Procedure to accommodate the relatively small sample size.

Examples 1 and 2 were both bicomponent spunbond nonwoven materials made in accordance with the teachings of U.S. Patent Application Publication 2004/0110442 to Rhim et al., referenced above. Example 1 included a thermoplastic urethane elastomeric component, and Example 2 included a styrenic block copolymer elastomeric component. The materials of Examples 1 and 2 each had a basis weight of approximately 0.8 ounces per square yard.

Example 3 was a thermoplastic urethane-based bicomponent spunbond nonwoven material made in accordance with the teachings of U.S. Pat. No. 6,225,243, referenced above. The material of Example 3 had a basis weight of approximately 0.75 ounces per square yard.

The Huggies® diaper front fastening patch includes a conventional loop material having substantially non-elastomeric engaging elements, and is included in the Example for comparison purposes. The patch comes from Huggies® diapers commercially available from Kimberly-Clark Corporation in 2004. The patch material can be made in accordance with the teachings of U.S. Pat. No. 5,858,515 to Stokes et al.

The Huggies® Pull-Ups® training pant side panel material includes substantially non-elastomeric engaging elements, and is included in the Example for comparison purposes. The side panel material comes from Huggies® Pull-Ups® training pants commercially available from Kimberly-Clark Corporation in 2004.

TABLE

Kinetic Coefficient of Friction: (grams)

| Code | Against Plexiglas ®-Type Plate | | Against Back Side of Hook | |
|---|---|---|---|---|
| | Avg | StdDev | Avg | StdDev |
| Example 1 | 0.72 | 0.03 | 0.77 | 0.07 |
| Example 2 | 0.74 | 0.11 | 0.63 | 0.05 |
| Example 3 | 0.58 | 0.02 | 0.62 | 0.06 |
| Huggies ® diapers front fastening patch | 0.27 | 0.01 | 0.57 | 0.03 |
| Huggies ® Pull-Ups ® training pants side panel material | 0.26 | 0.03 | 0.55 | 0.01 |

The data representatively illustrate that various loop-type fastening components in accordance with the present invention (Examples 1-3) exhibit higher kinetic coefficients of friction that conventional loop-type fastening components or attachment surfaces (Examples 4-5).

In particular embodiments, the female loop-type component of the present invention exhibits a kinetic coefficient of friction when rubbed against the Plexiglas®-type plate in accordance with the Coefficient Of Friction Test Method described below of at least about 0.4, more particularly at least about 0.5, more particularly at least about 0.6, still more particularly at least about 0.65, and still more particularly at least about 0.7 grams. In particular embodiments, the female loop-type component of the present invention exhibits a kinetic coefficient of friction when rubbed against the smooth back side of the hook material in accordance with the Coefficient Of Friction Test Method described below of at least about 0.6, more particularly at least about 0.65, more particularly at least about 0.7, still more particularly at least about 0.75, still more particularly at least about 0.8, still more particularly at least about 1.0, and still more particularly at least about 1.1 grams.

Coefficient of Friction Test Procedure

The kinetic coefficient of friction for loop-type fastening components is tested using ASTM method D 1894-00, incorporated herein by reference. The ASTM procedure requires a sample size of 250 mm in length and 130 mm in width. Single, continuous loop-type components of this size may not be present in conventional absorbent articles. Thus, to measure the coefficient of friction of loop-type components in actual absorbent articles, it may be necessary to modify the ASTM procedure to accommodate the reduced sample size. Such modifications may be readily accomplished by those of ordinary skill in the art.

The coefficient of friction of the loop-type component is tested by rubbing the loop-type component against either a Plexiglas®-type plate, or against the smooth back side of a piece of hook material. The Plexiglas®-type plate should be a sheet of PMMA (Polymethyl-methacrylate). Such Plexiglas®-type plates are available from CYRO Industries, Rockaway, N.J., U.S.A. The hook component is an 85 series buttressed palm tree shape mechanical fastening component having a smooth backing surface, available from Velcro USA, located in Manchester, N.H., U.S.A. A suitable testing apparatus is a properly calibrated Slip/Peel Tester module SP-101A, available from Instrumentors Supply, Inc., located in Utah, U.S.A.

As various changes could be made in the above exemplary embodiments of the invention without departing from the scope of the invention, it is intended that all matter contained in the above description and shown in the accompanying drawings shall be interpreted as illustrative and not in a limiting sense.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

We claim:

1. A mechanical fastening system comprising:
   a male component having a plurality of male engaging elements;
   a female component having a plurality of female engaging elements adapted for releasable direct engagement with the male engaging elements, wherein the female engaging elements comprise elastomeric fibers, wherein the elastomeric fibers together define a fibrous web.

2. The mechanical fastening system of claim 1, wherein the fibrous web is a woven material.

3. The mechanical fastening system of claim 1, wherein the fibrous web is a nonwoven material.

4. The mechanical fastening system of claim 3, wherein the fibrous web is a spunbond web.

5. The mechanical fastening system of claim 1, wherein the fibers are bicomponent fibers.

6. The mechanical fastening system of claim 5, wherein the fibers have an elastomeric core and a substantially non-elastomeric sheath.

7. The mechanical fastening system of claim 1, wherein the fibrous web has a coefficient of friction of at least about 0.5 grams when rubbed against a Plexiglas® material in accordance with the Coefficient Of Friction Test Method.

8. The mechanical fastening system of claim 1, wherein the fibrous web has a coefficient of friction of at least 0.65 grams when rubbed against a Plexiglass® material in accordance with the Coefficient Of Friction Test Method.

9. The mechanical fastening system of claim 1, wherein the fibrous web has a coefficient of friction of at least about 0.65 grams when rubbed against a smooth back side of a hook material in accordance with the Coefficient Of Friction Test Method.

10. The mechanical fastening system of claim 1, wherein the fibrous web has a coefficient of friction of at least 0.7 grams when rubbed against a smooth back side of a hook material in accordance with the Coefficient Of Friction Test Method.

11. The mechanical fastening system of claim 1, wherein the fibrous web is attached to a non-elastomeric base layer.

12. The mechanical fastening system of claim 1, wherein the fibrous web is substantially free of reticulated polyurethane foam material.

13. The mechanical fastening system of claim 1, wherein the fibrous web is substantially free of foam material.

14. A disposable absorbent article comprising:
a chassis comprising a bodyside liner and a garment-side outer cover,
an absorbent assembly sandwiched between the liner and the outer cover;
a mechanical fastening system comprising:
a male component having a plurality of male engaging elements;
a female component having a plurality of female engaging elements adapted for releasable direct engagement with the male engaging elements, wherein the female engaging elements comprise elastomeric fibers, wherein the elastomeric fibers together define a fibrous web.

15. The disposable absorbent article of claim 14, wherein the fibrous web is a woven material.

16. The disposable absorbent article of claim 14, wherein the fibrous web is a nonwoven material.

17. The disposable absorbent article of claim 16, wherein the fibrous web is a spunbond web.

18. The disposable absorbent article of claim 14, wherein the fibers are bicomponent fibers.

19. The disposable absorbent article of claim 18, wherein the fibers have an elastomeric core and a substantially non-elastomeric sheath.

20. The disposable absorbent article of claim 14, wherein the fibrous web has a coefficient of friction of at least about 0.5 grams when rubbed against a Plexiglas® material in accordance with the Coefficient Of Friction Test Method.

21. The disposable absorbent article of claim 14, wherein the fibrous web has a coefficient of friction of at least 0.65 grams when rubbed against a Plexiglas® material in accordance with the Coefficient Of Friction Test Method.

22. The disposable absorbent article of claim 14, wherein the fibrous web has a coefficient of friction of at least about 0.65 grams when rubbed against a smooth back side of a hook material in accordance with the Coefficient Of Friction Test Method.

23. The disposable absorbent article of claim 14, wherein the fibrous web has a coefficient of friction of at least 0.7 grams when rubbed against a smooth back side of a hook material in accordance with the Coefficient Of Friction Test Method.

24. The disposable absorbent article of claim 14, wherein the fibrous web is attached to a non-elastomeric base layer.

25. The disposable absorbent article of claim 14, wherein the fibrous web is substantially free of reticulated polyurethane foam material.

26. The disposable absorbent article of claim 14, wherein the fibrous web is substantially free of foam material.

27. The disposable absorbent article of claim 14, wherein the fibrous web is integral with the outer cover.

28. The disposable absorbent article of claim 27, wherein the first and second fibrous webs are respectively bonded to the first and second side panels.

29. The disposable absorbent article of claim 14, wherein the fibrous web is integral with the liner.

30. The disposable absorbent article of claim 14, wherein the disposable absorbent article further comprises first and second side panels extending from opposite lateral sides of the absorbent chassis, wherein a first fibrous web is disposed on the first side panel and a second fibrous web is disposed on the second side panel, wherein the first and second fibrous webs are respectively disposed on the first and second side panels.

* * * * *